United States Patent [19]

Diehr

[11] Patent Number: 5,164,508
[45] Date of Patent: Nov. 17, 1992

[54] PROCESS FOR THE PREPARATION OF N-(2-CHLORO-PYRIDIN-5-YL-METHYL)-ETHYLENEDIAMINE

[75] Inventor: Hans-Joachim Diehr, Wuppertal, Fed. Rep. of Germany

[73] Assignee: Bayer Aktiengesellschaft, Leverkusen, Fed. Rep. of Germany

[21] Appl. No.: 751,380

[22] Filed: Aug. 28, 1991

[30] Foreign Application Priority Data

Sep. 5, 1990 [DE] Fed. Rep. of Germany ....... 4028047

[51] Int. Cl.$^5$ ................. C07D 213/38; C07D 213/57
[52] U.S. Cl. ..................................... 546/329; 546/330
[58] Field of Search ........................... 546/329, 330

[56] References Cited

U.S. PATENT DOCUMENTS 2,675,383  4/1954  de Benneville ............... 558/346
2,868,795  1/1959  Cislak ........................... 546/329

FOREIGN PATENT DOCUMENTS 3603100  8/1987  Fed. Rep. of Germany.
52-28937  3/1977  Japan.

OTHER PUBLICATIONS

Mariella et al. "The Synthesis of Some Isomeric Dimethyl-hydroxymethylpyridines," J. Am. Chem. Soc. 71. p. 331–333. 1949.
Perez-Medina et al. "The Preparation and Reactions of Some Polysubstituted Pyridines," J. Am. Chem. Soc. 69. p. 2574–2578. 1947.
Chemical Abstracts, Band 87, No. 3, Jul. 18, 1977 "N-Substituted Aminoacetonitriles as Fungicides".
Chemical Abstracts, Band 94, No. 13, Mar. 30, 1981, "Aminonitriles".
Degering, E. An Outline of Organic Nitrogen Compounds 1945. University Lithoprinters. pp. 202–203.
R. Schroter: Amine durch Reduktion, pp. 554–569. 1957, Stickstoff-Verbindungen II.
Reduktion, Teil I, 1980, pp. 127–132.

*Primary Examiner*—C. Warren Ivy
*Assistant Examiner*—P. G. Spivack
*Attorney, Agent, or Firm*—Sprung Horn Kramer & Woods

[57] ABSTRACT

The present invention relates to a new process for the preparation of N-(2-chloro-pyridin-5-yl-methyl)-ethylene-diamine of the formula (I)

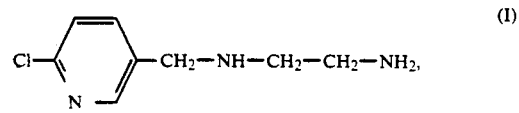

in a technically simple manner in high yield and in very good quality. The new process is characterized in that N-(2-chloro-pyridin-5-yl-methyl)-aminoacetonitrile of the formula (II)

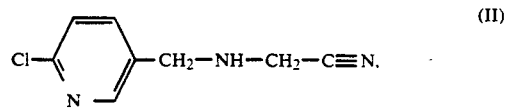

is reacted with hydrogen in the presence of ammonia and in the presence of a catalyst and also in the presence of a diluent, at temperatures between 0° C. and 100° C. and a pressure between 1 bar and 100 bar.

N-(2-Chloro-pyridin-5-yl-methyl)-ethylenediamine (I) can be used as an intermediate for the preparation of insecticides.

8 Claims, No Drawings

PROCESS FOR THE PREPARATION OF N-(2-CHLORO-PYRIDIN-5-YL-METHYL)-ETHYLENEDIAMINE

The invention relates to a new process for the preparation of N-(2-chloro-pyridin-5-yl-methyl)-ethylenediamine and to N-(2-chloro-pyridin-5-yl-methyl)-aminoacetonitrile as a new intermediate for this purpose.

It has been disclosed that N-(2-chloro-pyridin-5-yl-methyl)-ethylenediamine, an intermediate for insecticides, is obtained when 2-chloro-5-chloromethyl-pyridine is reacted with ethylenediamine in acetonitrile (cf. EP-A 163,855, Example 1).

However, the course of this reaction is not sufficiently selective, which results in a reduction in yield of the desired product.

Catalytic hydrogenation of corresponding aminoacetonitrile derivatives is known as a general method for the preparation of ethylenediamine derivatives. Halogen substituents—and generally also hydrocyanic acid—located on heteroaromatic components are, however, readily cleaved off in this process; in total, the selective course of the hydrogenation process—if at all successful to a satisfactory extent in each individual case—is usually highly dependent on the observance of certain reaction conditions (if appropriate, high pressure/high temperature/specific costly catalyst, etc.) (cf. Houben-Weyl, Methoden der organischen Chemie [Methods in Organic Chemistry], Volume IV/1c (1980), p. 127–132; loc. cit. Volume XI/1 (1957), p. 554–567).

A process has now been found for the preparation of N-(2-chloro-pyridin-5-yl-methyl)-ethylenediamine of the formula (I)

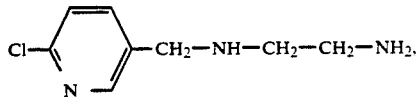

which is characterised in that N-(2-chloro-pyridin-5-yl-methyl)-aminoacetonitrile of the formula (II)

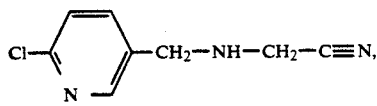

is reacted with hydrogen in the presence of ammonia and in the presence of a catalyst and also in the presence of a diluent, at temperatures between 0° C. and 100° C. and a pressure between 1 bar and 100 bar.

Surprisingly, the process according to the invention allows N-(2-chloro-pyridin-5-yl-methyl)-ethylenediamine to be obtained in a technically simple manner in high yield and in very good quality, that is to say, without the above-described shortcomings.

By providing N-(2-chloro-pyridin-5-yl-methyl)-aminoaceto-nitrile of the formula (II), which is employed as starting compound, a novel inventive route of obtaining N-(2-chloro-pyridin-5-yl-methyl)-ethylenediamine (I), which is known, is available.

The process according to the invention therefore represents a valuable enrichment of the prior art.

The course of the reaction in the process according to the invention can be represented by the following equation:

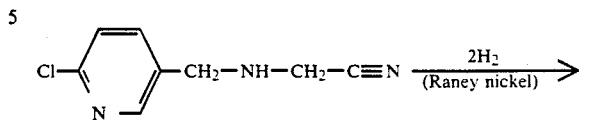

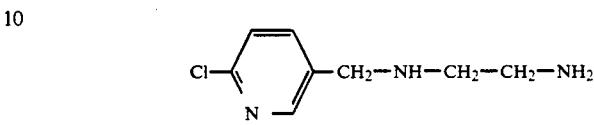

N-(2-Chloro-pyridin-5-yl-methyl)-aminoacetonitrile, which is to be used as starting substance in the process according to the invention, was hitherto not known from the literature and is also a subject of the present invention.

N-(2-Chloro-pyridin-5-yl-methyl)-aminoacetonitrile of the formula (II)

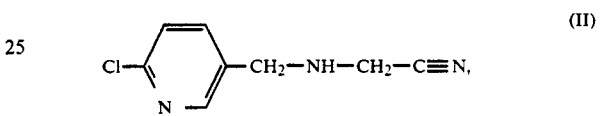

which is new, is obtained when 2-chloro-5-aminomethylpyridine of the formula (III)

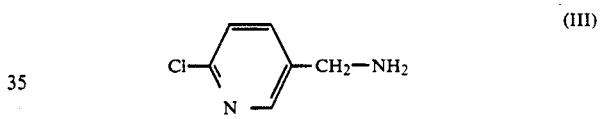

is reacted with formaldehyde in the presence of water and, if appropriate, in the presence of a reaction auxiliary such as, for example, sodium hydrogen sulphite, and the product is then reacted with a cyanide of the series comprising hydrocyanic acid, sodium cyanide or potassium cyanide, at temperatures between 0° C. and 50° C.

The compound of the formula (II) can furthermore be obtained from 2-chloro-5-chloromethyl-pyridine and aminoacetonitrile in the presence of bases.

2-Chloro-5-aminomethyl-pyridine of the formula (III), which is required as starting substance, has already been disclosed (cf. EP-A 302,389).

The process according to the invention for the preparation of N-(2-chloro-pyridin-5-yl-methyl)-ethylenediamine is carried out in the presence of a diluent. Suitable diluents in this context are virtually all customary solvents, as long as they are inert to hydrogen. The following are preferably employed as solvents: alcohols such as methanol, ethanol, propanol, isopropanol, butanol, isobutanol, sec-butanol and tert-butanol, in particular ethanol, ethers such as diisopropyl ether, diisobutyl ether, glycol dimethyl ether, diglycol dimethyl ether, tetrahydrofuran or dioxane, or esters, such as methyl acetate or ethyl acetate.

The process according to the invention is carried out in the presence of a catalyst. Suitable catalysts for this purpose are the customary catalysts to be used in catalytic hydrogenations. Examples which may be mentioned are Raney nickel, platinum, rhodium and palladium—the latter substances, if appropriate, on suitable carrier materials such as (active) charcoal or barium sulphate. Raney nickel is preferably employed as the catalyst.

When carrying out the process according to the invention, the reaction temperatures can be varied within a substantial range. In general, the process is carried out at temperatures between 0° C. and 100° C., preferably at temperatures between 10° C. and 50° C., in particular between 15° C. and 30° C.

In general, the process according to the invention is carried out in a pressure range between 1 bar and 100 bar, preferably between 2 bar and 50 bar, in particular between 5 bar and 20 bar.

For carrying out the process according to the invention, between 1 and 50 mol, preferably between 2 and 20 mol, of ammonia, between 10 and 200 g, preferably between 20 and 100 g of catalyst and hydrogen until it is no longer taken up, are generally employed per mole of N-(2-chloropyridin-5-yl-methyl)-aminoacetonitrile of the formula (II).

The process according to the invention is carried out under the conditions customary in the case of catalytic hydrogenations. In a preferred embodiment, the starting compound of the formula (II) is initially introduced in the diluent, the catalyst and ammonia are added, and the mixture is then treated with stirring in an autoclave with hydrogen until further consumption of hydrogen can no longer be detected. When the hydrogenation has ended, the catalyst is separated off by filtration and the solvent is carefully removed from the filtrate by distillation under reduced pressure. The residue which remains essentially contains the product of the formula (I).

N-(2-Chloro-pyridin-5-yl-methyl)-ethylenediamine, which is to be prepared by the process according to the invention, can be used as an intermediate for the preparation of insecticides (cf. EP-A 163,855).

The following equation for the further reaction to obtain insecticidal active compounds may be given by way of example:

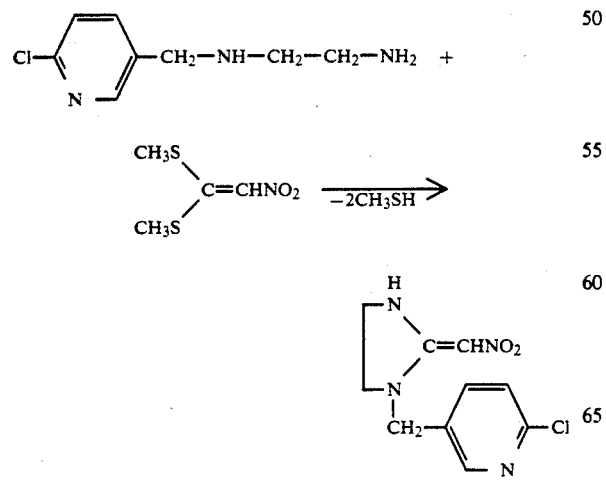

PREPARATION EXAMPLES
Example 1

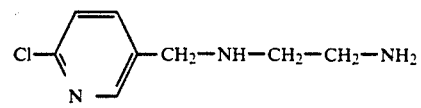

9.1 g (0.05 mol) of N-(2-chloro-pyridin-5-yl-methyl)aminoacetonitrile are dissolved in 75 ml of ethanol, and 3.6 g of Raney nickel and then 8 ml of liquid ammonia are added. In an autoclave, the mixture is stirred for 3 hours at 20° C. to 25° C. under a hydrogen pressure of approx. 10 bar. The catalyst is then separated off by filtration with suction, and the solvent is carefully removed from the filtrate by distillation under a water pump vacuum.

7.8 g (84% of theory) of N-(2-chloro-pyridin-5-yl-methyl)-ethylenediamine are obtained as a yellow oily residue. Boiling point: 125° C.–127° C./0.01 mbar.

Starting Compound of the Formula (II)

Example (II-1)

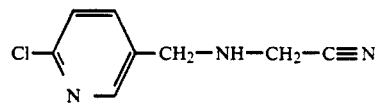

144 g (1 mol) of 2-chloro-5-aminomethyl-pyridine are added to a mixture of 260 g of an aqueous sodium hydrogen sulphite solution (1 mol NaHSO$_3$) and 100 g of an aqueous formaldehyde solution (1 mol H$_2$CO), and the mixture is stirred for 105 minutes at 25° C. to 30° C. A saturated aqueous solution of 49 g (1 mol) of sodium cyanide is then added and the mixture is stirred for 15 hours at 20° C. to 25° C. The aqueous solution is subsequently shaken twice with 250 ml portions of methylene chloride, and the combined organic extracts are dried using sodium sulphate and filtered. The solvent is carefully removed from the filtrate by distillation under a water pump vacuum.

164 g (90% of theory) of N-(2-chloro-pyridin-5-yl-methyl)-aminoacetonitrile are obtained as a yellow oily residue of refractive index $n_D> = 1.5520$.

I claim:

1. Process for the preparation of N-(2-chloro-pyridin-5-yl-methyl)-ethylenediamine of the formula (I)

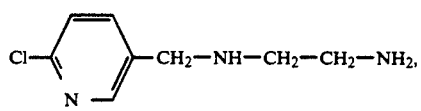

(I)

characterised in that N-(2-chloro-pyridin-5-yl-methyl)-aminoacetonitrile of the formula (II)

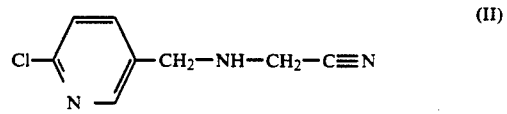

(II)

is reacted with hydrogen in the presence of ammonia and in the presence of a hydrogenation catayalst selected from the group consisting of Raney nickel, platinum, rhodium and palladium, and also in the presence of a diluent, at temperatures between 0° C. and 100° C. and a pressure between 1 bar and 100 bar.

2. Process according to claim 1, characterised in that the reaction is carried out in the presence of a solvent which is inert to hydrogen, selected from the group consisting of alcohols, ethers and esters.

3. Process according to claim 1, characterised in that the process is carried out in a temperature range from 10° C. to 50° C.

4. Process according to claim 1, characterised in that the reaction is carried out in a pressure range from 2 bar to 50 bar.

5. Process according to claim 1, characterised in that between 1 and 50 moles of ammonia, between 10 g and 200 g of catalyst and hydrogen until it is no longer taken up are employed per mole of N-(2-chloro-pyridin-5-yl-methyl)-aminoacetonitrile of the formula (II).

6. Process according to claim 1, characterised in that between 2 and 20 moles of ammonia, between 20 g and 100 g of catalyst and hydrogen until it is no longer taken up are employed per mole of N-(2-chloro-pyridin-5-yl-methyl)-aminoacetonitrile of the formula (II).

7. Process according to claim 1, characterised in that N-(2-chloro-pyridin-5-yl-methyl)-aminoacetonitrile (II) is initially introduced in the diluent, the catalyst and ammonia are added, and the mixture is then treated with stirring in an autoclave until further consumption of hydrogen can no longer be detected, and, when the hydrogenation has ended, the catalyst is separated off by filtration and the solvent is removed from the filtrate by distillation under reduced pressure.

8. N-(2-Chloro-pyridin-5-yl-methyl)-aminoacetonitrile of the formula (III)

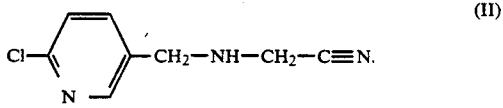

(II)

* * * * *

UNITED STATES PATENT AND TRADEMARK OFFICE
CERTIFICATE OF CORRECTION

PATENT NO. : 5,164,508

DATED : November 17, 1992

INVENTOR(S) : Hans-Joachim Diehr

It is certified that error appears in the above-identified patent and that said Letters Patent is hereby corrected as shown below:

Col. 6, line 14    Delete " formula (III) " and substitute -- formula (II) --

Signed and Sealed this

Twenty-eighth Day of June, 1994

*Attest:*

BRUCE LEHMAN

*Attesting Officer*    *Commissioner of Patents and Trademarks*